United States Patent
Luetkenhaus et al.

(10) Patent No.: US 10,794,798 B2
(45) Date of Patent: Oct. 6, 2020

(54) DEVICE FOR ASSESSING THE SILLAGE OF FRAGRANCE MATERIALS

(71) Applicant: Symrise AG, Holzminden (DE)

(72) Inventors: Matthias Luetkenhaus, Uslar (DE); Aurélien Saint-Paul, Paris (FR); Marco Singer, Holzminden (DE); Sophie Bensamou, New York, NY (US); Céline Carrasco, Saint Germain en Laye (FR)

(73) Assignee: Symrise AG, Holzminden (DE)

( * ) Notice: Subject to any disclaimer, the term of this patent is extended or adjusted under 35 U.S.C. 154(b) by 79 days.

(21) Appl. No.: 16/089,025

(22) PCT Filed: May 1, 2016

(86) PCT No.: PCT/EP2016/059715
§ 371 (c)(1),
(2) Date: Sep. 27, 2018

(87) PCT Pub. No.: WO2017/167407
PCT Pub. Date: Oct. 5, 2017

(65) Prior Publication Data
US 2019/0128782 A1 May 2, 2019

Related U.S. Application Data

(60) Provisional application No. 62/316,028, filed on Mar. 31, 2016.

(51) Int. Cl.
*G01N 1/22* (2006.01)
*A01N 25/18* (2006.01)
(Continued)

(52) U.S. Cl.
CPC ........... *G01N 1/22* (2013.01); *G01N 33/0001* (2013.01)

(58) Field of Classification Search
CPC .. G01N 1/22; G01N 33/0031; G01N 33/0001; G01N 30/02; G01N 30/7206;
(Continued)

(56) References Cited

U.S. PATENT DOCUMENTS 3,618,359 A 11/1971 Randebrock et al.
2006/0288871 A1* 12/2006 Crapser ................... A61L 9/127
96/52

(Continued)

*Primary Examiner* — Brandi N Hopkins
(74) *Attorney, Agent, or Firm* — Dilworth & Barrese, LLP

(57) ABSTRACT

Suggested is a device for assessing the sillage of fragrance materials, comprising or consisting of the following parts: (i) an evaluation tube (1) that is open on both ends; (ii) a ventilation system (2); (iii) at least two lockable sniffing ports (3a, 3b . . . ); (iv) a sample port (4); (v) a sample plate (5) and optionally (vi) a sample holder (6) whereby (a) said evaluation tube (1) is aligned horizontally and equipped with said at least two sniffing ports (3) and said sample port (4); (b) the front opening of said evaluation tube (1) is equipped with said ventilation system (2); (c) at least one sniffing port (3a) is located in the front section and at least one sniffing port (2b) is located in the rear section of said evaluation tube (3); (d) said sample port (4) is located within the front section of said evaluation tube (1); and (e) said sample port (4) has a diameter allowing to introduce either the sample plate (5) or the sample holder (6) into the evaluation tube (1).

17 Claims, 9 Drawing Sheets

(51) Int. Cl.
*G01N 1/40* (2006.01)
*G01N 33/00* (2006.01)

(58) Field of Classification Search
CPC .......... G01N 30/84; G01N 2030/8411; G01N 30/78; G01N 2030/8809; A61L 9/01; A61L 9/127; C11B 9/0061; C11B 9/0019; C11B 9/0015
See application file for complete search history.

(56) References Cited

U.S. PATENT DOCUMENTS

| | | |
|---|---|---|
| 2009/0320559 A1 | 12/2009 | Lemieuvre et al. |
| 2011/0236267 A1* | 9/2011 | Cox .................. G01N 33/0031 422/93 |
| 2011/0243788 A1* | 10/2011 | Garten .................... A61L 9/122 422/4 |
| 2012/0131986 A1 | 5/2012 | Varanasi et al. |

* cited by examiner

DEVICE FOR ASSESSING THE SILLAGE OF FRAGRANCE MATERIALS

BACKGROUND OF THE INVENTION

Field of Invention

The present invention belongs to the area of fragrances and refers to a device developed for measuring the sillage values of a fine fragrance or fragrance raw materials and a respective assessment method.

State of the Art

Sillage describes the ability of a perfume to emanate from a moving wearer and penetrate a room with its fragrance. The sillage performance is evaluated as
(i) an olfactory intensity and
(ii) as analytically determined concentration of VOCs in air.

Currently sillage is only referred to as a personal or anecdotal experience of fine fragrance performance, however, state of the art fails providing a method or device that allows quantifying of sillage of fragrances or fragrance raw materials by sensory and analytical means.

It has been the object of the present invention to close this gap in order to obtain additional information of the performance of new fragrance materials and fragrance compositions.

SUMMARY OF THE INVENTION

Object of the present invention is a device for assessing the sillage of fragrance materials, comprising or consisting of the following parts:
(i) an evaluation tube (1) that is open on both ends;
(ii) a ventilation system (2);
(iii) at least two lockable sniffing ports (3a, 3b . . . );
(iv) a sample port (4);
(v) a sample plate (5) and optionally
(vi) a sample holder (6)
whereby
(a) said evaluation tube (1) is aligned horizontally and equipped with said at least two sniffing ports (3) and said sample port (4);
(b) the front opening of said evaluation tube (1) is equipped with said ventilation system (2);
(c) at least one sniffing port (3a) is located in the front section and at least one sniffing port (2b) is located in the rear section of said evaluation tube (3);
(d) said sample port (4) is located within the front section of said evaluation tube (1); and
(e) said sample port (4) has a diameter allowing to introduce either the sample plate (5) or the sample holder (6) into the evaluation tube (1).

The device is capable of imitating trailing of a fragrance and getting reliable information about the sillage of any fine fragrance or fragrance raw material in short time using analytical means as well as the sensory perception of trained individuals.

BRIEF DESCRIPTION OF THE DRAWINGS

The invention will be described in greater detail with reference to the accompanying drawings, in which.

DETAILED DESCRIPTION OF THE INVENTION

In the following preferred embodiments of the device are described in order to illustrate, but not to limit the invention.

Tube

The fragrance evaluation tube (1) is typically made of a long glass cylinder that is open on both ends (alternatively the tube can be made of metal, plastic or other materials that show low interaction with VOCs). It is aligned horizontally and displays at least two, preferably in total four sniffing ports, two in the front section and two in the rear section. These sniffing ports can be used alternatively to adapt analytic instruments (for example SPME fibre, TENAX tube and pump, FAIMS etc.). The front opening is connected to a ventilation system that applies a defined air flow to the tube. Preferably, the front section also encompasses a sample holder that allows introducing the perfumed sample on a glass plate inside of the tube. The term "front section" refers to the part of the tube starting from the opening where ventilator and sample are placed until the middle of the tube. Rear section means the part of the tube beyond.

Figure 1A:
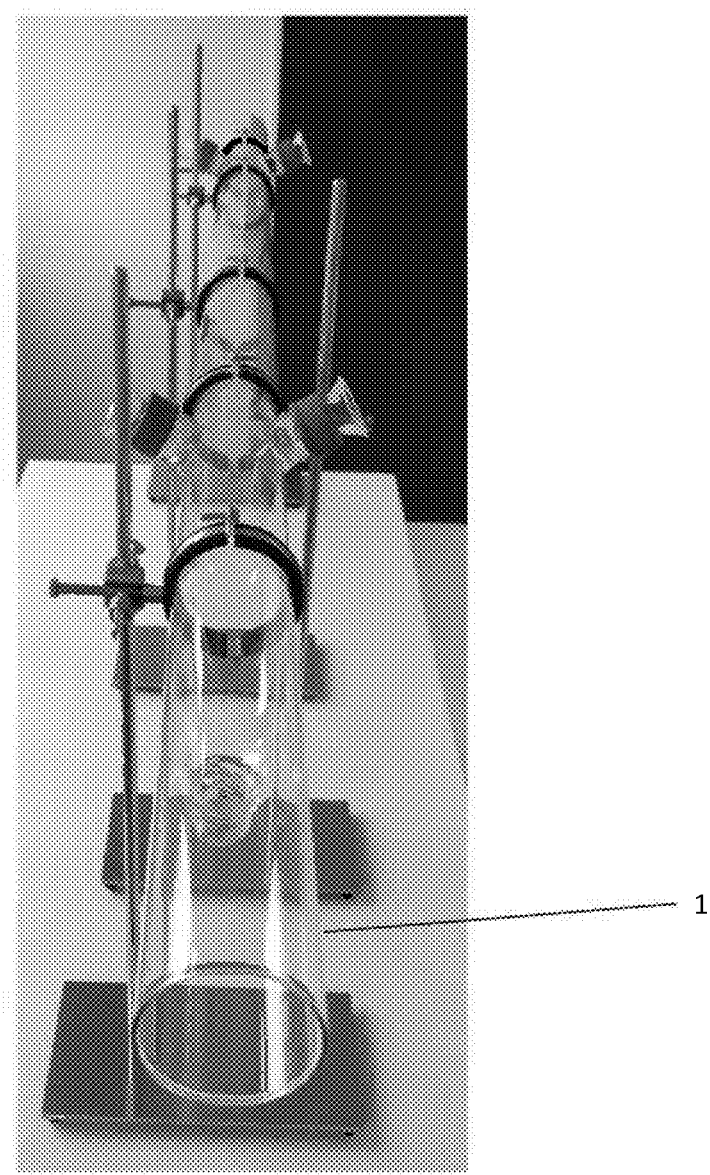
FIG. 1A illustrates a perspective view of an evaluation tube in accordance with the present invention.
Figure 1B:
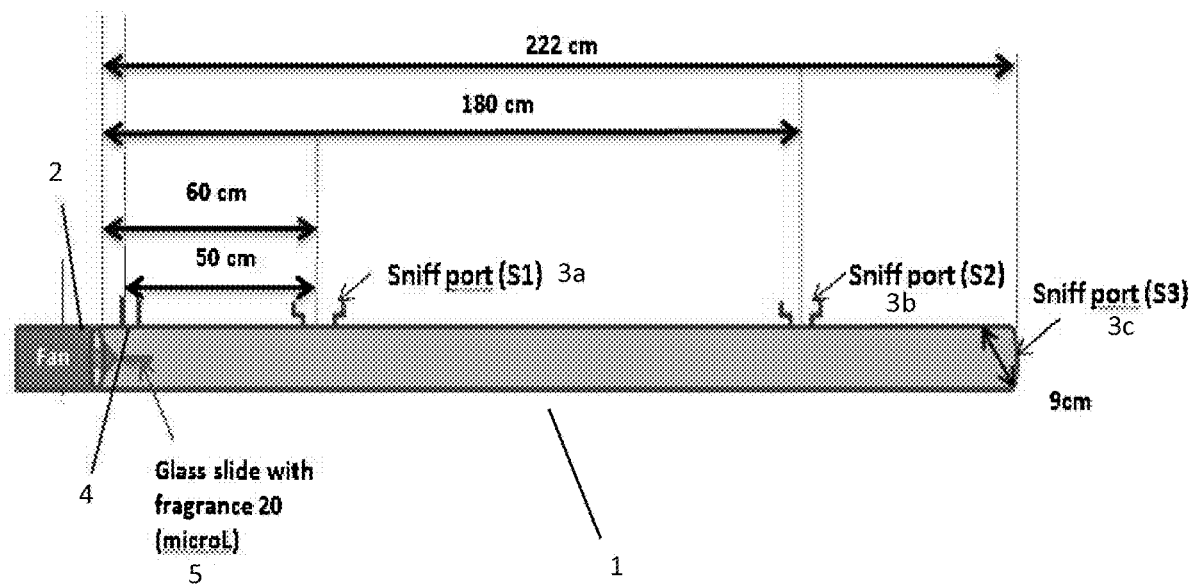
FIG. 1B schematically illustrates length and positioning of components of the evaluation tube.

FIG. 1A provides a photo of a suitable tube; FIG. 1B a typical example for length and diameter of a tube and the position of the sample and sniffing ports. Typically the tube has a length of from about 150 to about 250 cm, and a diameter of from about 5 to about 20 cm.

Ventilation

The ventilator consists of a plastic support fitted with a fan. Furthermore it encompasses an electronic device to regulate the fan speed. The air flow is around $2.10^{-4}$ m/h.

Figure 2A:
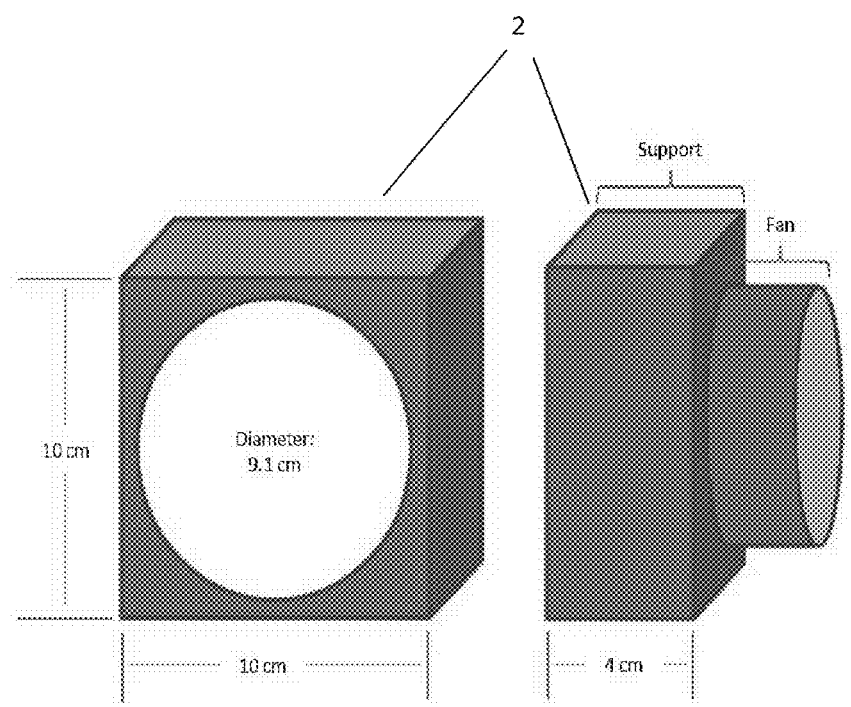
FIG. 2A schematically illustrates dimensions and positioning of components forming a ventilation system in accordance with the present invention.
Figure 2B:
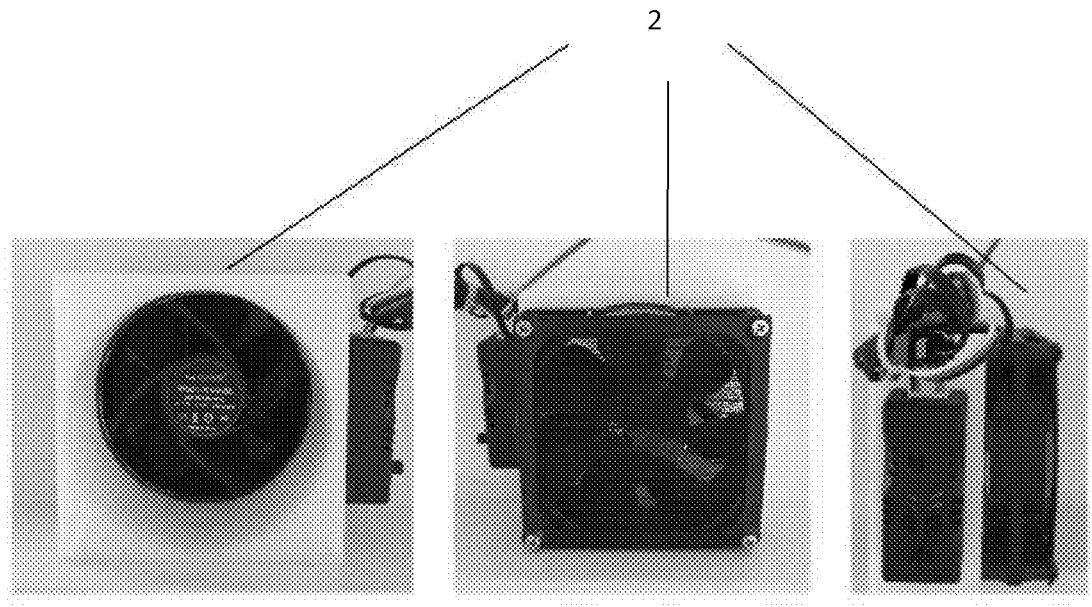
FIG. 2B illustrates several views of the ventilation system for use in accordance with the present invention.

FIG. 2A shows a drawing of the ventilator, FIG. 2B some photos.

Sniffing Ports

The sniffing ports are connected via a screw cap (Schott GL 45) with a hole and a rubber fitting. The ports can be closed completely with a regular screw cap (GI 45) if needed or other devices (analytic instrumentation) can be connected via appropriate adaptors (SPME fibres, TENAX tubes, FAIMS etc.)

Figure 3A:
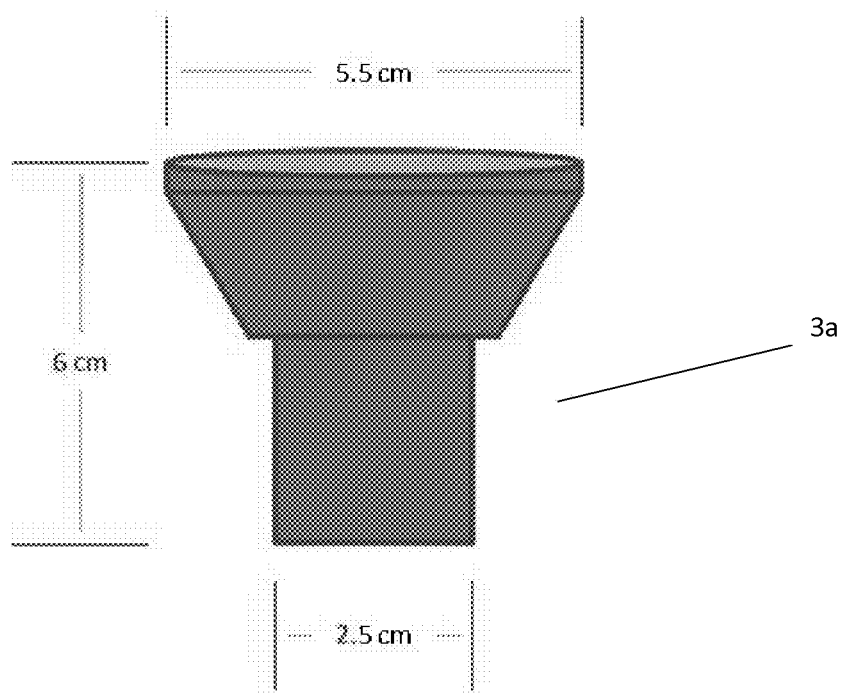
FIG. 3A schematically illustrates dimensions of a sniffing port in accordance with the present invention.
Figure 3B:
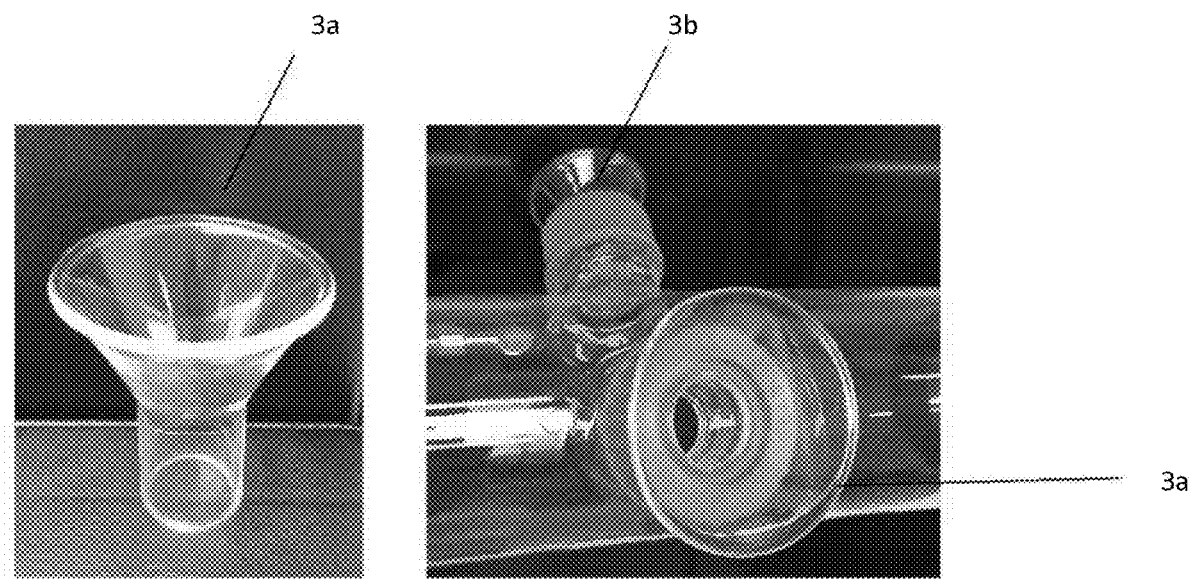
FIG. 3B illustrates perspective views of the sniffing port as used in the present invention.

FIG. 3A shows a drawing of the sniffing port, FIG. 3B some photos).

Sample Holder

Figure 4A:
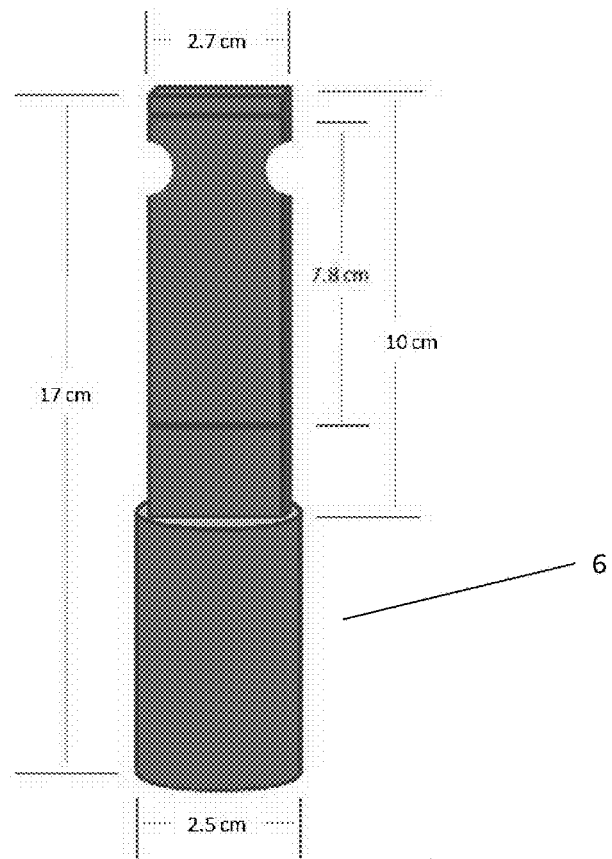
FIG. 4A schematically illustrates dimensions of a sample holder in accordance with the present invention.
Figure 4B:
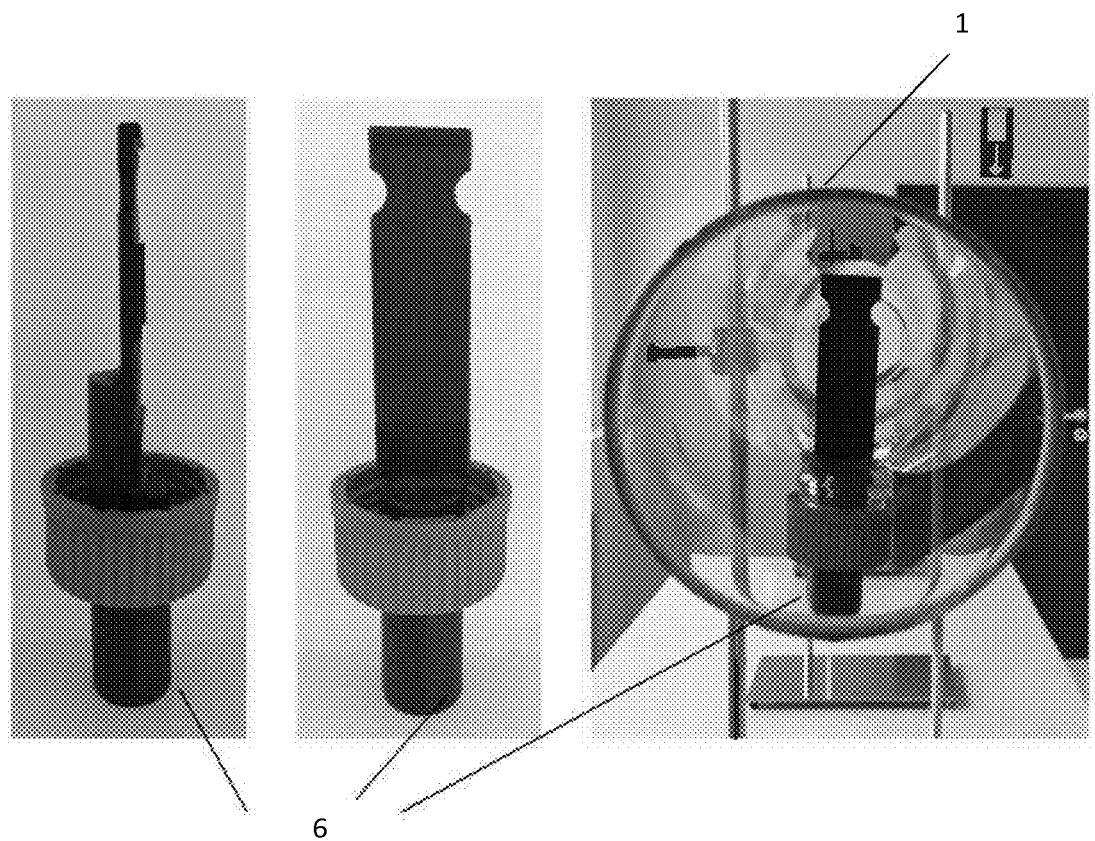
FIG. 4B illustrates perspective views of the sample holder as used in the present invention.

The sample holder carries a glass plate (not displayed here) with the sample to be analyzed. It is introduced via the sample port in the front section of the tube and fixed with a screw cap (Schott GL45) shown in the pictures below. The sample holder is inserted in the air flow such as the glass plate faces the fan. FIG. 4A shows a drawing of the sample holder, FIG. 4B some photos.

The test is designed to assess the sillage intensity profile of a fine fragrance over time. It mirrors closely the behavior on human skin in terms of fragrance profile and loss of intensity.

Samples can also be introduced without the sample holder simply by placing the glass plate carrying the perfume horizontally in the tube.

Sample Plate

Figure 5:
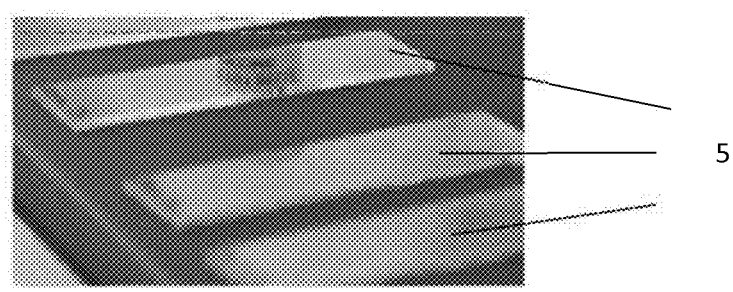
FIG. 5 illustrates a perspective view of a sample supported on sample plates in accordance with the present invention.

The sample are supported on sample plates (75×25 mm, see FIG. 5) that carry 20 μL of perfume solution (EdT or EdP) or fragrance raw materials diluted in solvent (EdT base). Typically the plates are made from glass. Alternatively the sample can be presented on other supports e.g. artificial skin, plastic or metal supports that do not interact strongly with the sample or display a similar release of fragrances than real human skin. Several supports were evaluated for measuring the performance of fine fragrances over a time period of 6 to 8 h. Samples were kept at elevated temperature or ambient temperature in a ventilated space and evaluated regarding i) absolute intensity and ii) similarity of olfactive profile as compared to real skin. The results are summarized in the following Table 1:

highest similarity to the olfactive profile of the FFs on real skin. The most similar was the artificial skin, closely followed by the glass slides.

Alternatively the support for the sample can be made of other materials like plastic, metal or coated variants thereof that mimic the intensity and hedonic profile of real skin.

Method

Another object of the present invention relates to a method for assessing the sillage of fragrance materials using the device of claim 1 and comprising or consisting of the following steps:

(a) providing a fragrance material and placing it on the sample plate (5);

(b) introducing the perfumed sample plate through the sample port (4) into the evaluation tube (1);

(c) starting the ventilation system (2) to provide a constant and defined air flow through the tube;

(d1) connecting at least one sniffing port (3) with an analytic instrument capable for objective determination of the intensity of fragrance; and/or (d2) opening at least one sniffing port (3) for subjective determination of the intensity of fragrance by a trained individual (e) analysing the data obtained from step (d1) and/or (d2).

Preferably said sample plate (5) is mounted on a sample holder (6) and both are introduced through the sample port (4) into the evaluation tube (1).

Typically about 10 to about 50 μL and in particular about 20 μL fragrance material is placed on the sample plate (5). Usually the perfumed sample plate (5) is heated to about 25 to about 35° C. and subsequently cooled down to ambient temperature before introducing it into the tube. The method is described in more detail in the experimental part of the specification.

TABLE 1

Sample supports

| Support | Fragrances | Description |
|---|---|---|
| Real skin (reference) | Fragrance A (EdT for female) Fragrance B (EdT for Male) | One male and one female carrier were chosen to wear the FF on the upper fore arm. A total of 20 μL of the sample was applied on one side on an area of 3 cm × 1.5 cm) with a varipette and equally distributed. Carriers had to keep their sleeves up during the test. |
| Blotters | Fragrance A (EdT for female) Fragrance B (EdT for Male) | Both samples were applied on a blotter (large blotters) with a varipette (20 μL) and were kept at ambient temperature. |
| Cups | Fragrance A (EdT for female) Fragrance B (EdT for Male) | Standard board cups (0.2 l) with a tissue (20 × 20 cm, TORK facial tissue) were used. Sample was applied on different spots of the tissue (20 μl). |
| Artificial skin | Fragrance A (EdT for female) Fragrance B (EdT for Male) | Artificial skin from IMS (Vitro-skin ®) was mounted on a 250 ml Erlenmeyer containing 100 ml water. The upper diameter of skin covered lid was 6 cm. A sample of 20 μl was applied by varipette and the Erlenmyers were kept in a heated water bath such as the skin was tempered at 32° C. (checked with surface thermometer). |
| Glass plates | Fragrance A (EdT for female) Fragrance B (EdT for Male) | Standard microscopy slides were kept at 32° C. with 20 μl of sample. |

Figure 6A:
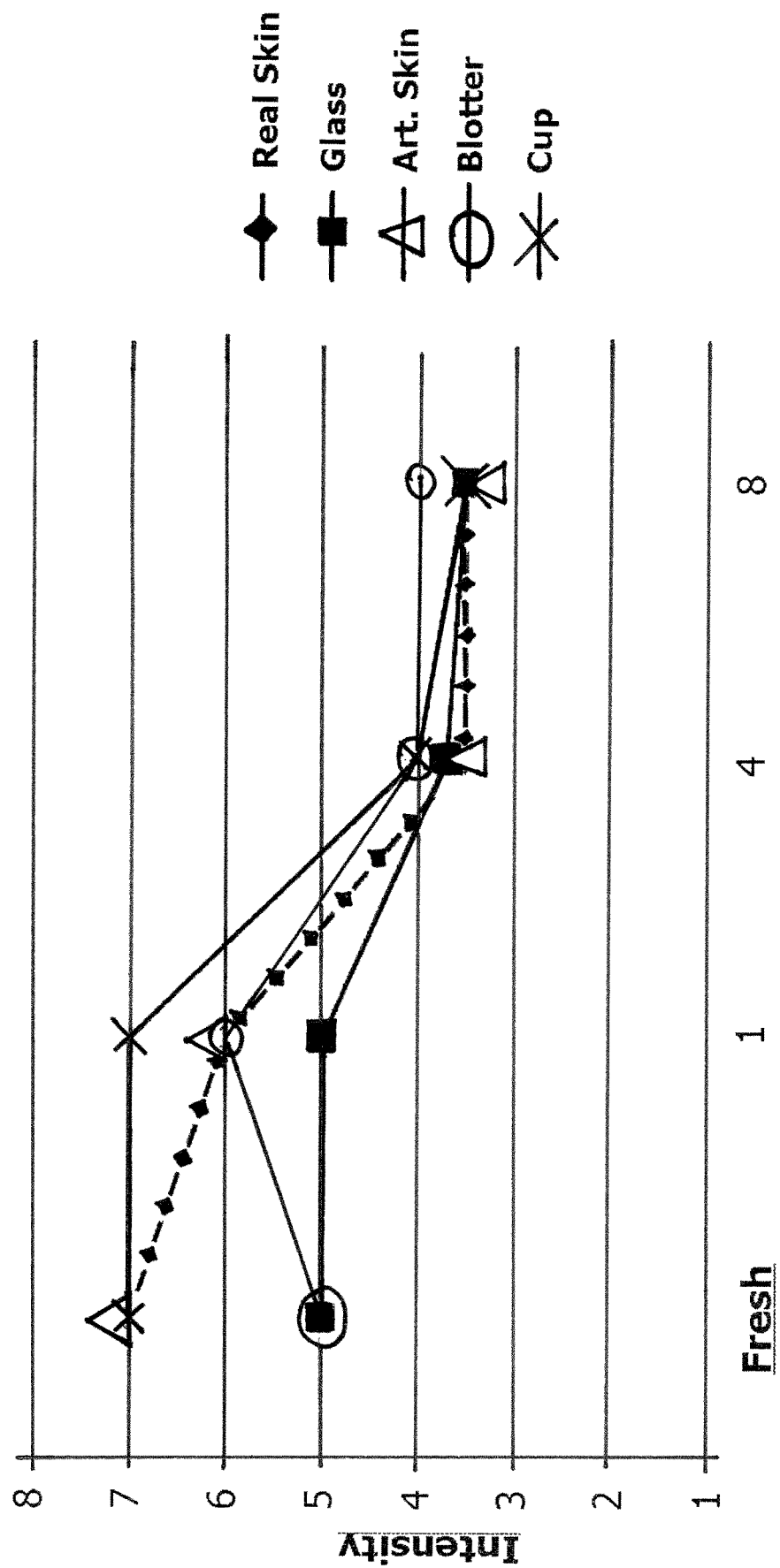
FIG. 6A is a graph of an intensity profile of a fragrance assessed in accordance with the present invention.
Figure 6B:
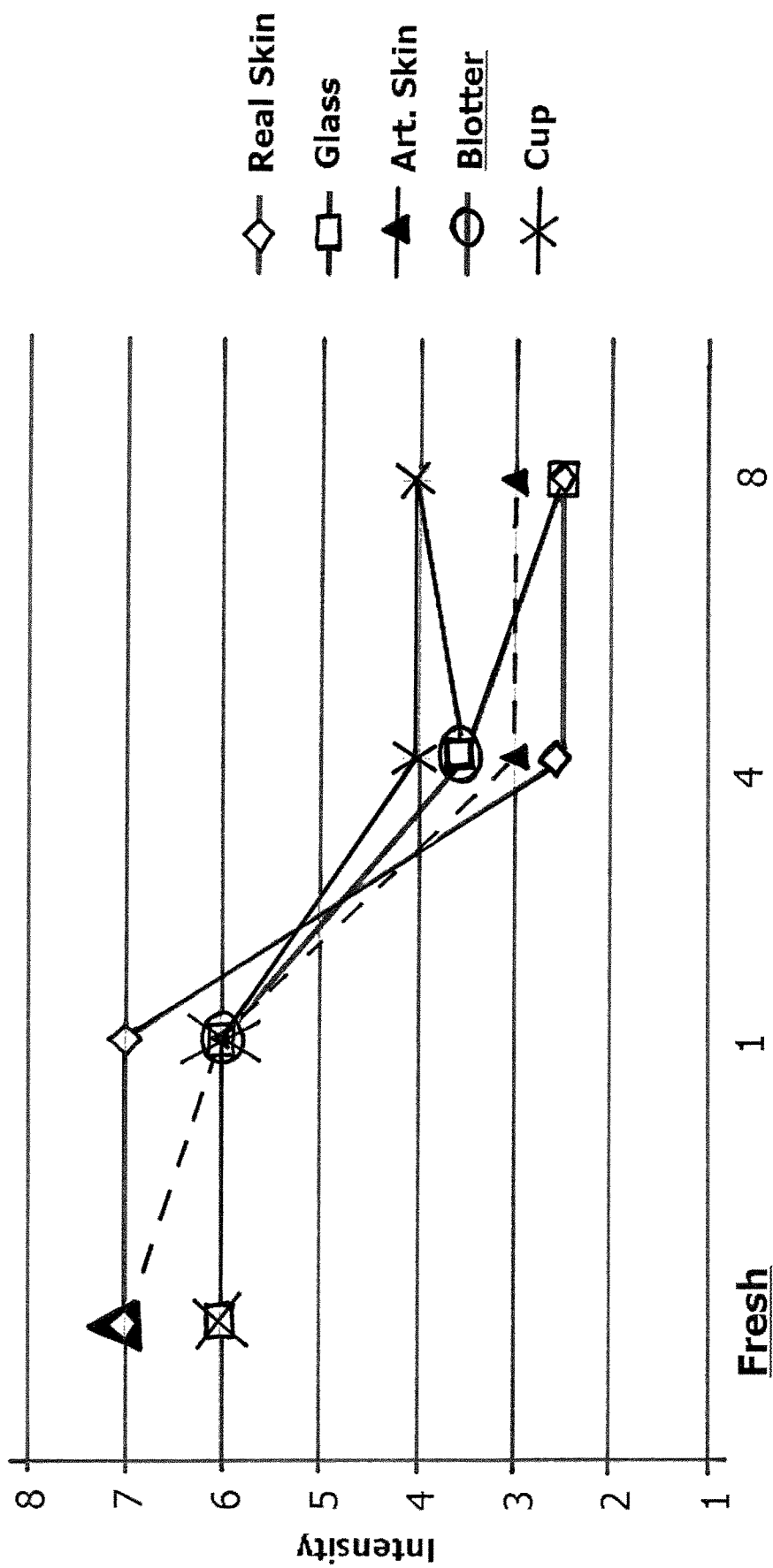
FIG. 6B is a graph of an intensity profile of another fragrance assessed in accordance with the present invention.

The results are compiled in FIGS. 6A and 6B. The intensity profiles were quite similar but it seems that the artificial skin and the glass plates mirrors the intensity profiles of real skin best. These supports also show the Industrial Application Another object of the present invention is directed to the use of the device explained above for assessing the sillage of a fragrance material.

EXAMPLES

Example 1

Sillage Method: General Procedure

The following procedure illustrates the method according to the invention by an example, without limiting the protection accordingly.

In brief the fine fragrance sample is applied to a glass plates which is heated to 32° C. for up to 3 h. The sample is placed in a glass tube to which a defined air flow is applied and the intensity is evaluated by a trained panel on a labeled magnitude scale (LMS). The results are plotted on a graph as intensity ratings over time. FIGS. 6A and 6B show the intensity traces of fragrances A and B over the time (in h).

Materials
Representative fine fragrance sample (it is important to know if it's a EdT or EdP, ideally confirmed by lab analysis with exact dosage)
Glass plates (approx. 75×25 mm)
Hot plate (that can be regulated to 32° C.)
Micropipette (for 20 μL)
Intensity standards for the scale
IT tools to record panelists ratings
Ideally a contactless thermometer to check the surface temperature of samples
Specific tube designed for this kind of evaluation (see plan page 3)+4 funnels (Height (mm): 6±(0.5 mm) Width (mm):±6(0.5 mm)
Anemometer to check the air flow in the tube (Anemometer PCE-423)
Tachometer PCE-DT 63
Protocol The hotplate is set to 32° C. and the temperature variance is checked with a surface thermometer. Deviations within +/−1° C. can be tolerated. Regions on the plate that do not fulfill this requirement should not be used to heat the samples.

The fan is placed at one end of the tube at 60 cm from S1 (see scheme); the air flow variance is checked with a Tachometer. Before each evaluation, the RPM of the fan should be checked. We should have about 766 RPM. Deviations within +/−30 RPM are tolerated.

Micro-slides are placed on the hotplate such as they are not in contact with each other.

It is recommended to use 2 micro-slides on top of each other if the hotplate has an off odor that contaminates the evaluation samples.

Each slide is loaded with 20 μL of the fine fragrance with the help of a micropipette. Care has to be taken that the sample does not contaminate the hot plate.

Samples can be prepared in different ways for the evaluation i) either to be all evaluated at the same time or ii) to be evaluated throughout the time of storage This procedure is more appropriate for being tested with a panel that is only available for a certain time in a day (e.g. 4 pm-4:30 pm). It allows only testing of 1 FFs (2 times T0 and T3 h) per session. The tube should be clean between each evaluation. Slides are prepared such as at the end of the maximum storage time (3 h) all samples can be evaluated during the global evaluation (3 h, Fresh). E.g. the session should occur at 2 pm then the 3 h sample is applied at 11 am. The fresh sample is applied on a heated slide and immediately removed from the hot plate. Samples are evaluated from the weakest (3 h) to the strongest (fresh) in order to minimize adaptation. Nevertheless extensive pausing between the individual micro-slides is recommended.

This procedure is more appropriate if the panelists are available throughout the day to evaluate samples at T0 (fresh) and at T3 h. It allows testing of 1-2 FFs per session but requires the panelists to strictly respect the given time intervals. Slides are prepared at a given time and evaluated Samples are left to cool down to ambient temperature (5 min) before evaluation. For the 2 procedures the sample should be introduced in the tube when all panelists are present. Panelists should evaluate the fragrance during the same period of time (max 5 min after the beginning of the test).

Sillage intensity of the fragrance is evaluated by an expert trained panel. Sample is placed at 50 cm from S1, the fan at 60 cm from S1 (Only one sample is evaluated in the tube at the same time). The fan is turned on and panelists have to wait 3 min before to smell at the different Sniff ports. Parameter for the fan (XT Power Unit −9 volts; Wiring: USB plug(5V); Fan Lowest Setting-rpm)

This time allows us to have a balanced state in the tube. After these 3 min, panelists are asked to evaluate the intensity of the fragrance at the different Sniff ports (S1, S2, and S3) on the right side of the tube when you are positioned on the side of the tube. Between each evaluation, the tube must be clean by using alcohol or ethanol and air. After this step, the tube has to be odorless.

When the tube is ready, panelists have 3 min to do the evaluation, after this time it's recommended to stop the evaluation because the intensity of the fragrance will be different.

Panelists are required to use the standards when attributing their rating on the LMS scale.

Evaluations are performed on the sniffing ports in the front section and in the rear section to obtain public sillage and intimate sillage values respectively.

All results of important benchmarks are collected in a database.

Example 2

Perfume Performance (Sillage and Long-Lastingness)

Figure 7:
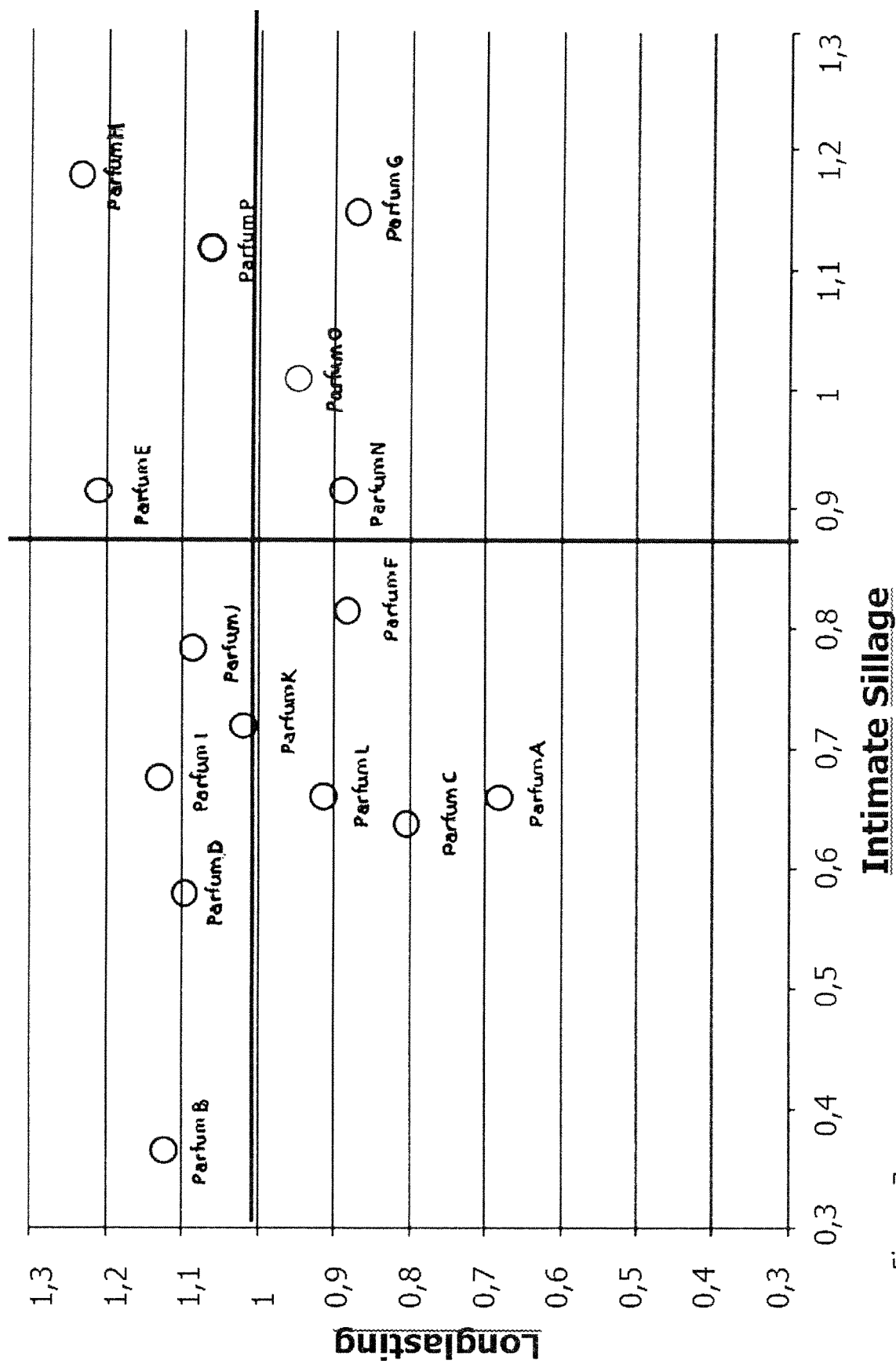
FIG. 7 is a graph of intimate sillage vs. long-lastingness of fragrances assessed in accordance with the present invention.
Figure 8:
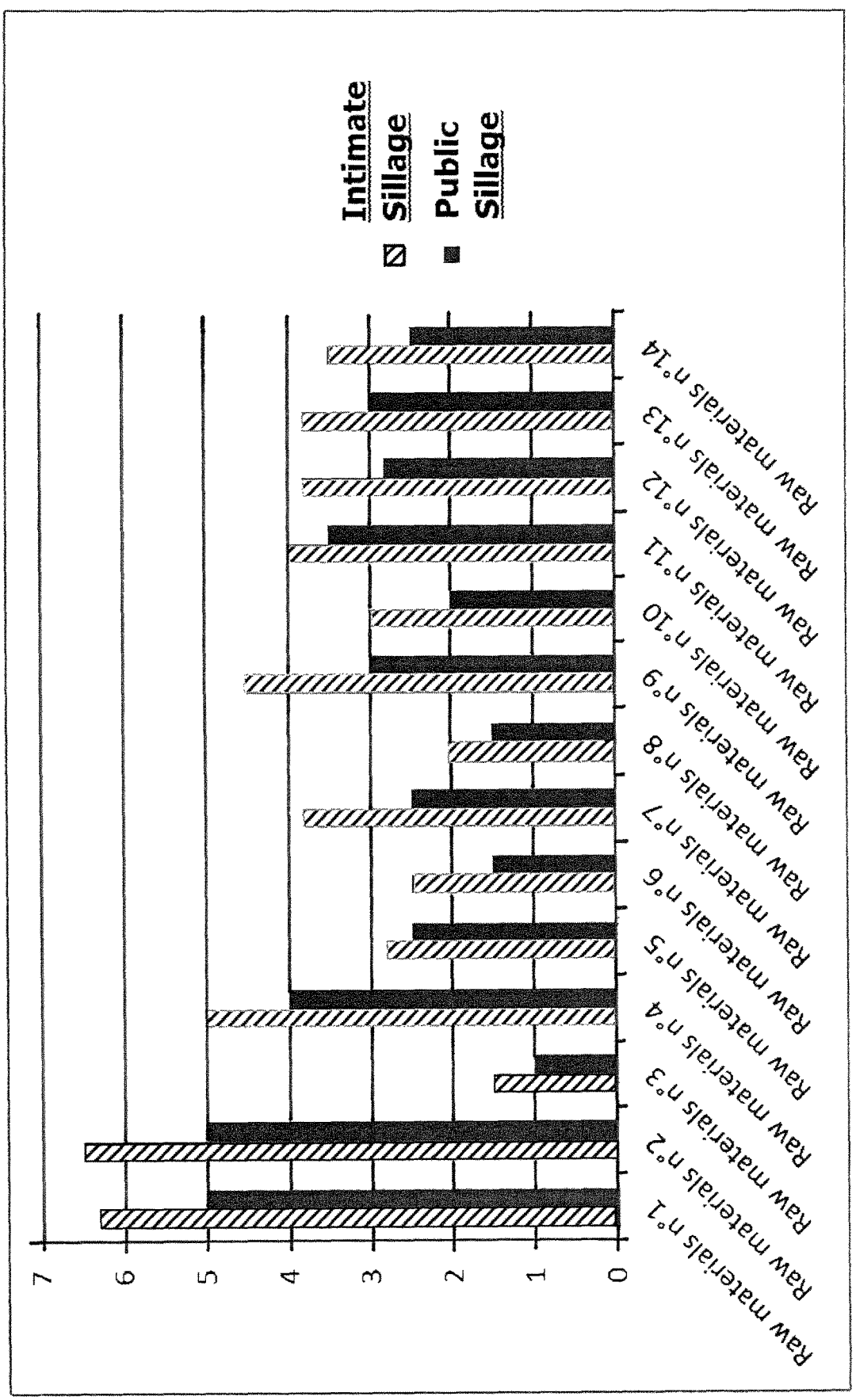
FIG. 8 is a graph of intimate and public sillage of raw fragrance materials assessed in accordance with the present invention.

The x-axis displays the ISV (intimate sillage value, higher values indicate better performance) and the y-axis reflects the long-lastingness (higher values indicate better long-lastingness). Highly performing fragrances are found in the upper right quadrant of the diagram (Perfume E, H and P). The results are shown in FIG. 7. Individual ISVs and PSVs (intimate and public sillage values respectively) for a subset of raw materials are depicted in FIG. 8.

The invention claimed is:

1. A device for assessing the sillage of fragrance materials, comprising:
   an evaluation tube (1) that is open on both ends;
   (ii) a ventilation system (2);
   (iii) at least two lockable sniffing ports (3a, 3b . . . );
   (iv) a sample port (4);
   (v) a sample plate (5); and
   (vi) a sample holder (6) for holding the sample plate (5) wherein
   (a) said evaluation tube (1) is aligned horizontally and equipped with said at least two sniffing ports (3) and said sample port (4);
   (b) a front opening of said evaluation tube (1) is equipped with said ventilation system (2);
   (c) at least one lockable sniffing port (3a) is located in a front section of said evaluation tube (1) and at least one lockable sniffing port (3b) is located in a rear section of said evaluation tube (1);

(d) said sample port (4) is located within the front section of said evaluation tube (1);

(e) said sample port (4) has a diameter allowing introduction of either the sample plate (5) or the sample holder (6) into the evaluation tube (1); and (f) said device is configured to evaluate both public and intimate sillage values of the fragrance materials.

2. The device of claim 1, made of glass, metal or plastic.

3. The device of claim 1, wherein said evaluation tube (1) has a length of about 150 to about 250 cm.

4. The device of claim 1, wherein said evaluation tube (1) has a diameter of about 5 to about 20 cm.

5. The device of claim 1, wherein said evaluation tube (1) is equipped with 4 said lockable sniffing ports (3a to 3d), two of them located in the front section of said evaluation tube (1) and the other two in the rear section of said evaluation tube (1).

6. The device of claim 1, wherein said lockable sniffing ports (3) are equipped with screw caps and fittings to adapt analytic instruments.

7. The device of claim 1, wherein said plate (5) is made from glass or artificial skin.

8. The device of claim 1, wherein said plate (5) is a heated plate.

9. A method for assessing the sillage of fragrance materials using the device of claim 1 and comprising the steps of:

(a) providing a fragrance material and placing it on the sample plate (5);

(b) introducing the perfumed sample plate through the sample port (4) into the evaluation tube (1);

(c) starting the ventilation system (2) to provide a constant and defined air flow through the tube (1);

(d1) connecting at least one sniffing port (3) with an analytic instrument capable for objective determination of the intensity of fragrance; and/or (d2) opening at least one sniffing port (3) for subjective determination of the intensity of fragrance by a trained individual, and (e) analysing the data obtained from step (d1) and/or (d2), wherein step (e) comprises obtaining an intimate sillage value by performing an evaluation on the sniffing port (3a) in the front section, and/or obtaining a public sillage value by performing an evaluation on the sniffing port (3b) in the rear section.

10. The method of claim 9, wherein said sample plate (5) is mounted on a sample holder (6) and both are introduced through the sample port (4) into the evaluation tube (1).

11. The method of claim 9, wherein about 10 to about 50 μL fragrance material is placed on the sample plate (5).

12. The method of claim 9, wherein said perfumed sample plate (5) is heated to about 25 to about 35° C.

13. The method of claim 12, wherein the perfumed sample plate (5) is subsequently cooled down to ambient temperature before introducing into the tube.

14. The device of claim 1, wherein the lockable sniffing ports (3a, 3b) are each formed by an outwardly flared funnel situated on a tubular stem in turn mounted in a respective opening through the evaluation tube (1) and lockable thereto.

15. The device of claim 14, wherein the lockable sniffing ports (3a, 3b) are lockable to the evaluation tube (1) via a screw cap.

16. The device of claim 1, wherein the ventilation system (2) comprises a fan and a plastic support fit with the fan and, in turn, secured to the front end of the evaluation tube (1).

17. The device of claim 16, wherein the sample holder (5) is fixed to the front end of the evaluation tube (1) via a screw cap, and with the plastic support then secured to the front end of the evaluation tube (1).

* * * * *